(12) United States Patent
Clawson

(10) Patent No.: US 7,189,356 B1
(45) Date of Patent: Mar. 13, 2007

(54) OCCULT BLOOD TESTING APPARATUS WITH FEATURES FOR ENHANCING EASE OF USE

(75) Inventor: Burrell E. Clawson, Newport Beach, CA (US)

(73) Assignee: Diagnostica, Inc., Crofton, MD (US)

( * ) Notice: Subject to any disclaimer, the term of this patent is extended or adjusted under 35 U.S.C. 154(b) by 287 days.

(21) Appl. No.: 10/139,473

(22) Filed: May 3, 2002

(51) Int. Cl.
 *G01N 31/00* (2006.01)
(52) U.S. Cl. .............................. 422/56; 422/55; 422/58; 422/61; 422/102; 436/66
(58) Field of Classification Search .................. 422/55, 422/56, 58, 61, 102; 436/66; 435/4
See application file for complete search history.

(56) References Cited

U.S. PATENT DOCUMENTS

| | | | |
|---|---|---|---|
| 4,071,317 A | 1/1978 | Lam |
| 4,333,734 A | 6/1982 | Fleisher |
| 4,365,970 A | 12/1982 | Lawrence et al. |
| 4,382,064 A | 5/1983 | Detweiler et al. |
| D281,903 S | 12/1985 | Duffy |
| 4,562,043 A | 12/1985 | Mennen et al. |
| 4,582,685 A | 4/1986 | Guadagno et al. |
| 4,615,982 A | 10/1986 | Lawrence |
| 4,645,743 A | 2/1987 | Baker et al. |
| 4,738,823 A | 4/1988 | Engelmann |
| 4,789,629 A | 12/1988 | Baker et al. |
| 4,818,702 A | 4/1989 | Lawrence |
| 4,937,197 A | 6/1990 | Lawrence |
| 4,939,097 A | 7/1990 | Lawrence |
| 4,983,416 A | 1/1991 | Hunsinger et al. |
| 5,100,619 A | 3/1992 | Baker et al. |
| 5,106,582 A | 4/1992 | Baker et al. |
| 5,137,808 A | 8/1992 | Ullman et al. |
| 5,171,529 A | 12/1992 | Schreiber |
| 5,182,191 A | 1/1993 | Fan et al. |
| 5,196,167 A | 3/1993 | Guadagno et al. |
| 5,198,365 A | 3/1993 | Grow et al. |

(Continued)

FOREIGN PATENT DOCUMENTS

WO 00/08137 2/2000

*Primary Examiner*—Jill Warden
*Assistant Examiner*—Sam P. Siefke
(74) *Attorney, Agent, or Firm*—Stout, Uxa, Buyan & Mullins, LLP; Frank J. Uxa; Linda A. Fox

(57) ABSTRACT

A self-contained system for testing for the presence of occult blood in a specimen has been provided with features enhancing its ease of use. The system includes a housing holding a test matrix and a container for releasing a developing medium onto the test matrix. The housing includes a base portion encasing both the container and the test matrix, and a moveable cover for selectively covering and uncovering the base. The cover is provided with a tab which can be manipulated with a finger of one hand, and the base is provided with tabs which can be grasped easily with one or two other fingers of the same hand, thus allowing the cover to be easily opened and closed with one hand. Other ease-of-use features include an applicator with a tip configured for optimized retrieval and even spreading of the specimen on the test matrix, and indicia imprinted at various positions on the housing designating both the location and order in which the different steps of the testing procedure are to be performed.

7 Claims, 5 Drawing Sheets

U.S. PATENT DOCUMENTS

| | | |
|---|---|---|
| 5,217,874 A | 6/1993 | Guadagno et al. |
| 5,264,181 A | 11/1993 | Schreiber |
| 5,310,680 A | 5/1994 | Baker et al. |
| 5,344,762 A | 9/1994 | Karapetian |
| 5,391,498 A | 2/1995 | Baker et al. |
| 5,504,013 A | 4/1996 | Senior |
| 5,593,851 A * | 1/1997 | Jackson ................... 435/12 |
| 5,668,011 A * | 9/1997 | Jackson ................ 435/309.1 |
| 5,747,351 A * | 5/1998 | Hemmati ................ 436/514 |
| 5,840,584 A | 11/1998 | Waldenburg |
| 6,077,711 A | 6/2000 | Singer |

* cited by examiner

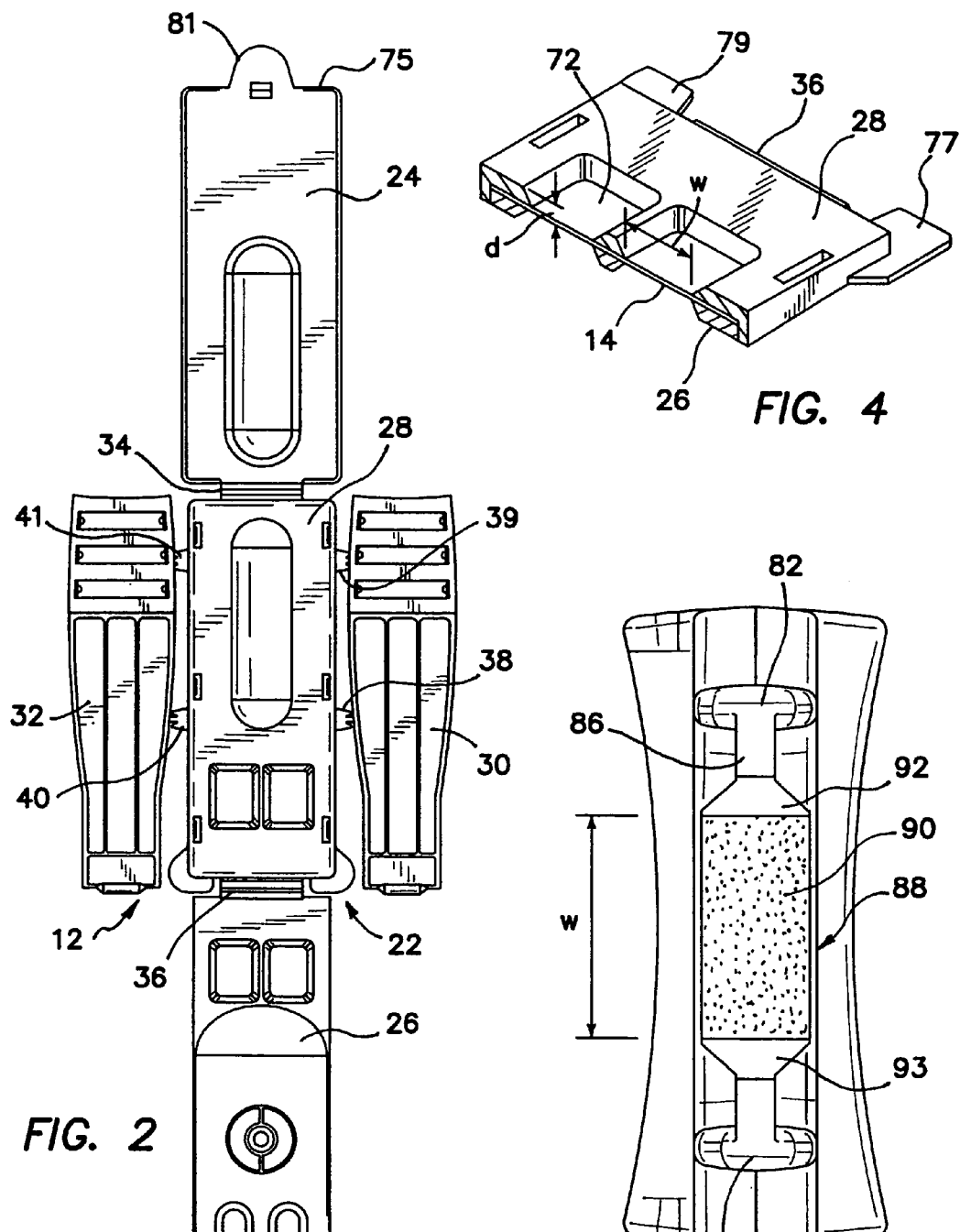

OCCULT BLOOD TESTING APPARATUS WITH FEATURES FOR ENHANCING EASE OF USE

BACKGROUND OF THE INVENTION

The present invention is directed to systems and methods useful in testing for occult blood in a fecal specimen. More particularly, the invention is directed to a testing apparatus which is suitable for at-home use by untrained individuals, as well as by clinicians in hospitals and doctor offices.

Over 140,000 new persons per year in the United States are afflicted with cancer of the colon and rectum, the disease occurring equally in both men and women. Contrary to many other forms of cancer, early diagnosis and treatment of colorectal cancer and its precursor polyps does result in a cure rate of 80% to 90%. If, however, the disease is not detected until the later stages, the cure rate drops significantly. Thus, early detection of the disease is important to successful treatment of colorectal cancer. For this reason, it is recommended that all individuals over age 50 with no family history of the disease be screened annually for colorectal cancers. Individuals with family history of the disease or other known risk factors should be screened annually beginning no later than age 40.

Conventional screening procedures consist of testing for occult (hidden) blood in stool samples provided by a patient. Typically, the patient must collect two separate specimens on a test card on each of three consecutive days, and then deliver the test cards to a laboratory. At the laboratory, a physician or lab technician applies developer liquid to each specimen's test matrix, which has previously been impregnated with a suitable chromogenic reagent, such as guaiac. If blood is present in the specimen, the chromogenic reagent will cause the test matrix to change colors when the developer fluid is added, indicating that fecal occult blood or a similar reactant has been found.

One factor deterring individuals from undergoing their recommended annual screening is the natural revulsion which many, if not most, people feel toward handling and looking at fecal matter. This revulsion may be amplified by the lack of a suitable implement for obtaining a specimen and applying it to the test matrix. Most test kits simply provide a wooden coffee-stirrer type stick which is somewhat difficult to manipulate and often, because of its generally smooth exterior surface, does not pick up a large enough sample or retain the sample without risk of dropping some of the fecal matter. Another unpleasant factor is the inconvenience and, sometimes, embarrassment associated with transporting or mailing the fecal matter specimens to a testing laboratory in a paper envelope.

In order to eliminate or reduce the aforementioned problems, various attempts have been made to develop a convenient test kit which requires a minimum of handling of fecal specimens, and can be performed by an untrained individual in the privacy of his or her own home. Examples of such attempts are disclosed in U.S. Pat. Nos. 4,582,685 and 5,196,167 to Guadagno et al., and U.S. Pat. No. 5,840,584 to Waldenburg. None of these prior art test kits have successfully met all of the needs of in-home users, however, and none has been approved by the FDA for over-the-counter sale.

To date, the only fecal occult blood testing kit which has been approved by for the FDA for over-the-counter sale is a kit manufactured by Diagnostica, Inc., of Las Vegas, Nev., features of which are disclosed in U.S. patent application Ser. No. 09/132,439 and International Application No. PCT/US99/17954. The Diagnostica kit comprises a container of free-standing developing medium, and a test matrix having a specimen placement area on one side. On the opposite side of the test matrix is a result area that generally coincides with the specimen placement area, and a control area that is longitudinally spaced from the result area. Both the container and the matrix are encased in a housing having a first pair of openings aligned with the specimen placement area, a second pair of openings aligned with the result area, and a third pair of openings aligned with the control area. A cover is provided for securely enclosing a specimen located on the specimen placement area. To test for occult blood, a user simply places fecal specimens in the openings aligned with the specimen placement area, closes the cover, compresses the housing to break the container and releases the developing medium. He or she then turns the housing over to look for appropriate color changes in the result and control areas.

The aforementioned Diagnostica test kit possesses numerous advantages over the prior art. The cover is particularly advantageous, since it keeps the fecal specimen out of the user's sight and prevents it from dropping off of leaking from the specimen placement area, even when the user inverts the housing to read the results. In addition, the kit can be disposed of easily and hygienically after testing, with no need for special handling.

Nonetheless, the Diagnostica kit disclosed in the aforementioned U.S. and International patent applications has some potential drawbacks. Users who have not performed the test before may have difficulty understanding or remembering the instructions and may perform the steps in the wrong order. In addition, some users may collect too little or too much sample on the stick provided with the kit, and have difficulty spreading it over the specimen placement area. Still others may find it difficult to open and close the cover of the housing with one hand while holding the specimen collection stick in the other hand.

Accordingly, it would be advantageous to provide an apparatus for testing for occult blood, for example, fecal occult blood, with features that enhance its ease of use by untrained individuals. Further, it would be advantageous to provide a hygienic and relatively simple test kit which reduces the need for manual dexterity, while providing accurate and reliable results.

SUMMARY OF THE INVENTION

A self-contained system for testing for the presence of occult blood in a specimen has been provided with features enhancing its ease of use. The system includes a housing holding a test matrix and a container for releasing a developing medium onto the test matrix. The housing includes a base portion encasing both the container and the test matrix, and a moveable cover for selectively covering and uncovering the base. The cover is provided with a tab which can be manipulated with a finger of one hand, and the base is provided with tabs which can be grasped easily with one or two other fingers of the same hand, thus allowing the cover to be easily opened and closed with one hand.

An applicator provided for use with the system includes a handle portion configured to be grasped by a user and a distal portion having an end configured for optimized retrieval and spreading of the specimen on the test matrix. In a preferred embodiment, the applicator comprises two identical applicator halves, one of which serves as the handle portion and the other of which serves as the distal portion. Connector elements are provided for joining the two halves together. For reasons of manufacturing convenience, the two halves are integrally formed with and frangibly connected to opposite sides of the system housing. To use the applicator, a user simply detaches the two applicator halves from the housing, assembles them end-to-end, then collects and applies the specimen as instructed.

The instructions for use are preferably embossed or otherwise printed on the various components of the system. These instructions preferably indicate both the order in which the steps of the testing procedure are to be performed, and the location for carrying out the steps. Thus, steps to be performed with the cover closed are provided on the cover, steps to be performed with the cover open are provided on the top portion of the base, and steps to be performed with the housing inverted (and the cover closed) are provided on the bottom portion of the base. This reduces the chance of any confusion on the part of the user, and increases the likelihood that the test will be performed correctly and accurate results obtained.

Each and every feature and combination of two or more features described herein is included within the scope of the present invention provided that the features included in the combination are not mutually inconsistent.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 2 is a plan view of the housing, cover, and applicator of the system before assembly;

FIG. 4 is an enlarged fragmentary perspective view showing a portion of the base of the system housing, with a portion broken away to show interior detail;

FIG. 9 is an enlarged end view of FIG. 7;

DETAILED DESCRIPTION OF THE DRAWINGS

Figure 1:
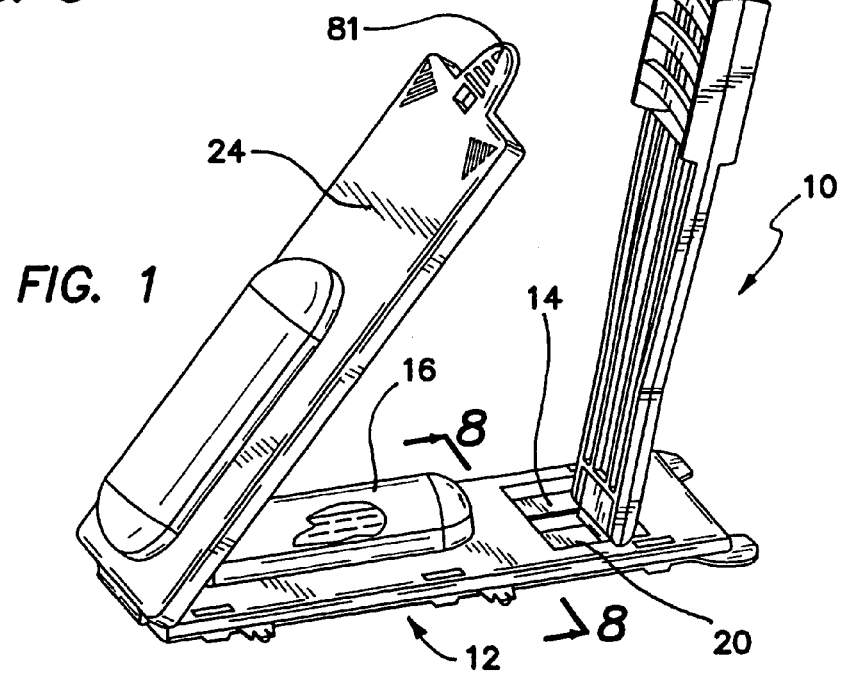
FIG. 1 is a perspective view of a system for testing for fecal occult blood in accordance with the present invention, with a portion broken away to show interior detail.

Referring now to the drawings, FIG. 1 shows a self-contained system 10 for testing for a reactant such as occult blood in a specimen of a spreadable substance such as fecal matter (not shown). The system comprises a housing 12 enclosing a test matrix 14 such as guaiac-treated paper (shown in FIG. 4), and a glass ampule 16 filled with a free-standing liquid developing medium such as liquid hydrogen peroxide/ethyl alcohol solution. An applicator 18 is provided for collecting the fecal matter specimen and applying it to a specimen placement area 20 on the test matrix 14.

Referring now to FIG. 2, the unassembled housing, which is preferably provided to the consumer in a hermetically sealed foil pouch (not shown), includes a base 22 and a cover 24. The base 22 has a bottom section 26 and a top section 28. Identical applicator halves 30 and 32 are coupled to opposite sides of the top section 28 of the base 22. In a preferred embodiment of the invention, the cover 24, bottom section 26, top section 28, and applicator halves 30, 32 are made from a unitary or single piece of plastic or polymer material. The cover 24, bottom base section 26, and top base section 28 are preferably flexibly and serially joined to one another by thinned hinge elements 34 and 36, while the applicator halves 30, 32 are frangibly connected to the top section 28 of the base 22 by weakened elements 38, 39, 40, and 41. Other embodiments of the invention may provide the applicator separately from the housing, for example, and/or in a single piece, as a pair of non-identical pieces or more than two pieces. Similarly, the cover and the sections of the base could be made of more than one piece, made of materials other than plastic, and/or have sections of other shapes.

Figure 3:
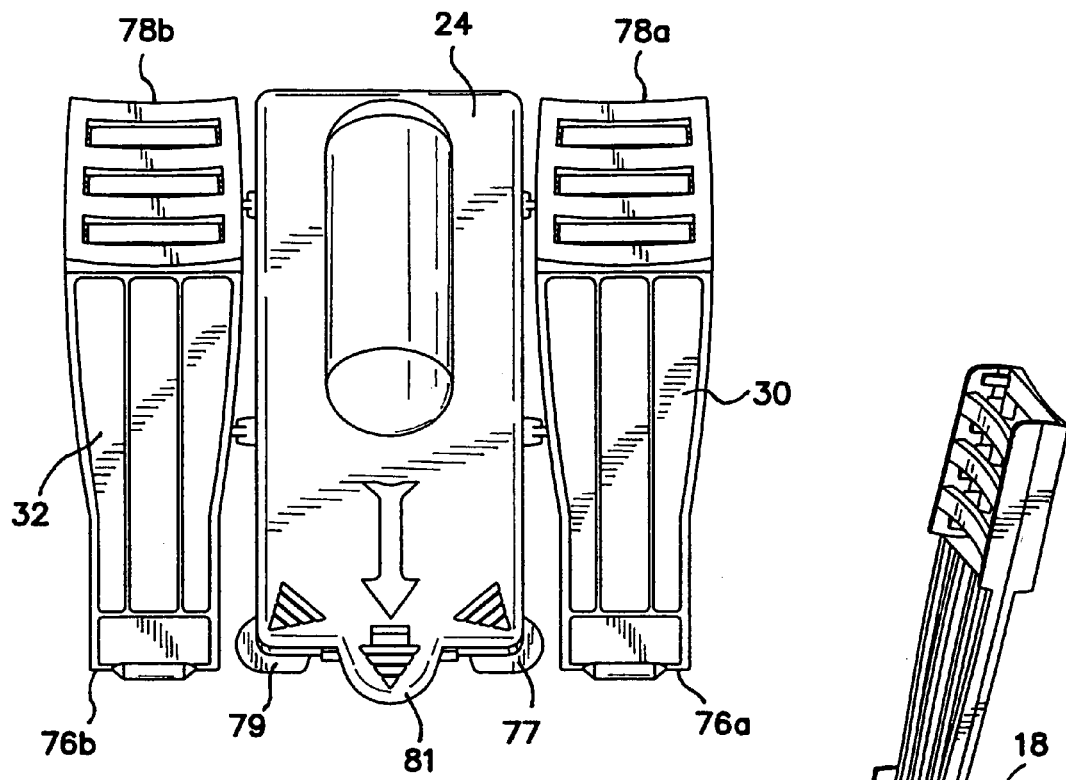
FIG. 3 is a plan view of the system after assembly.

FIG. 3 shows the system 10 in the form in which it is provided to the user. The test matrix and ampule have been placed underneath the top section 28 of the base 22, and the bottom section 26 has been folded up against the top section 28, locking the test matrix and ampule into position. The cover 24 has been latched over the specimen placement openings to prevent contamination of the test matrix during transport. The only portion of the system 10 which has not been preassembled is the applicator 18.

Figure 12:
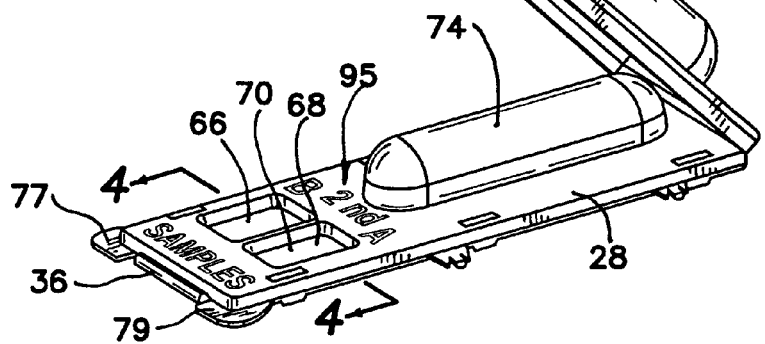
FIG. 12 is a bottom plan view of the housing according to the embodiment of FIG. 10.

Returning now to FIG. 2 with additional reference to FIG. 12, the bottom section 26 of the base 22 has two oblong openings 42, 44 near a first end 46. The oblong openings have beveled edges 48 for better viewing of the validation areas 50 of the test matrix 14. Two rectangular openings 52, 54 are provided near a second end 56 of the bottom section 26. The rectangular openings 52, 54 have beveled edges 58 for better viewing of the result areas 60 of the test matrix 14. A circular depression 62 is located in the second surface 51 intermediate the validation area viewing openings 42, 44 and the result area viewing openings 52, 54. A protuberance 64 is located in the center of the depression 62. The depression 62 decreases the rigidity of the bottom section 26 and enables a user to compress the ampule when the protuberance 64 is pressed against a hard, flat surface such as a table or counter top. It has been found that a depression 62 formed in the second surface 51 of the bottom section 26 reduces the amount of liquid needed to saturate the matrix relative to the amount that would be needed if the depression were formed in the first surface 49.

Figure 2A:
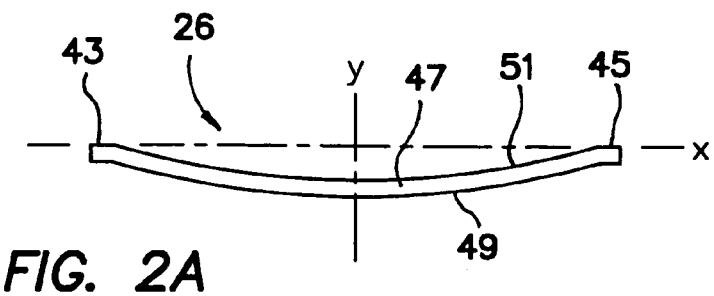
FIG. 2A is an enlarged end view of the bottom section of the housing before assembly.

FIG. 2A is an enlarged end view showing that the bottom section 26 of the base is slightly curved about a vertical axis of symmetry y. Specifically, the bottom section 26 has generally flat side edge portions 43, 45, and a central portion 47 including a first surface 49 and a second surface 51, both of which are somewhat concave with respect to the illustrated horizontal axis x. When the bottom section 26 is folded about the front hinge 36 and snapped into place underneath the top section 28, the curvature is flattened with respect to the horizontal axis x. Thus, the first surface 49 is urged against the center of the top section, compressing the test matrix and holding it securely in place. This minimizes the amount of open space between the top and bottom sections 26 and 28, which in turn further minimizes the amount of liquid needed to saturate the matrix in a given short period of time.

Figure 11:
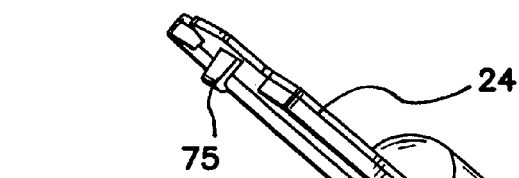
FIG. 11 is a perspective view of the housing according to the embodiment shown in FIG. 10, with the cover in an open position.

The top section 28 of the base 22, best shown in FIG. 11, includes two rectangular openings 66, 68 that align with specimen placement areas 70 on the text matrix 14, on the opposite side from the result areas 60 and result viewing openings 52, 54. An oblong ampule-holding dome 74 extends between the specimen placement openings 66, 68 and the end of the top section 28 near the rear hinge 34. Extending from the inner top wall of the dome 74 are two projections (not shown) which act in tandem with the depression 62 and protuberance 64 on the bottom section 26 to facilitate breaking of the ampule 16.

The front hinge 36 projects distally along the front of the section 28 and matingly receives a hook 75 depending from the underside of the cover 24 to latch the cover when necessary. A gripping arrangement comprising tabs 77, 79 and 81 (seen in FIG. 10) is provided for allowing a user to easily open and close the cover 24 with one hand while holding an applicator in the other hand. Specifically, the tabs 77, 79, which extend distally and laterally from the corners of the top section 28 on either side of the hinge 36, are structured for a user to hold between two fingers, for instance the thumb and middle finger, of one hand while pressing upwardly with another finger, for instance the index finger, of the same hand against the tab 81 extending distally from the front edge of the cover 24. Strictly speaking, only one tab 77 or 79 is required on the top section 28 of the base, since most users will be able to open the cover 24 using only the thumb and finger of one hand. However, two tabs 77, 79 are preferred, since such an arrangement is equally convenient for both right and left-handed users, and also for users with decreased manual dexterity or strength.

Figure 5:
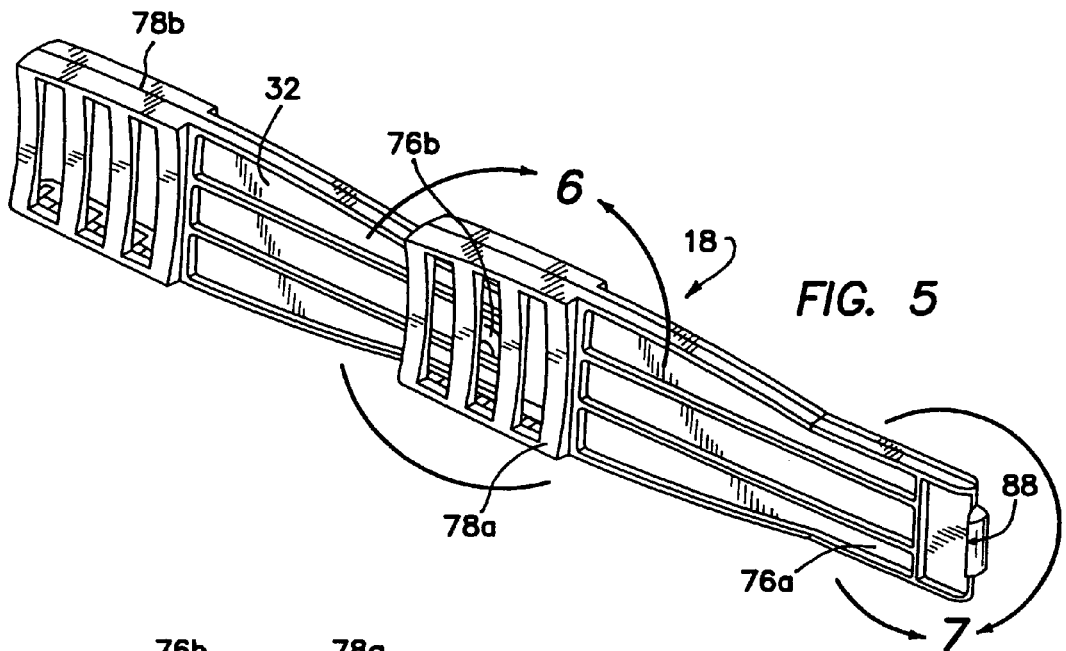
FIG. 5 is a perspective view of an applicator assembly in accordance with the present invention.
Figure 6:
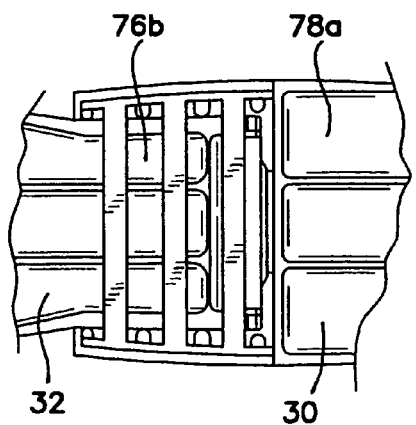
FIG. 6 is an enlarged plan view of the encircled area 6—6 of FIG. 5.

Referring again to FIG. 3, with additional reference to FIGS. 5 and 6, each of the applicator halves 30, 32 comprises a relatively narrow distal end 76a,b and a wider, hollow proximal end 78a,b. To assemble the applicator 10, the user simply detaches the two applicator halves 30, 32 from the sides of the base 28, and inserts the distal end 76b of one applicator half 32 into the hollow proximal end 78a of the other applicator half 30. A close fit between the distal end 76b of one applicator half 32 and the receiving proximal end 78a of the other applicator half 30 ensures that the halves 30, 32 will be securely joined.

When the applicator halves 30, 32 are assembled, the proximally positioned half 32 serves as a handle to be grasped by the user, while the distal end 76a of the distally positioned half 30 serves as a collector and spreader.

Figure 8:
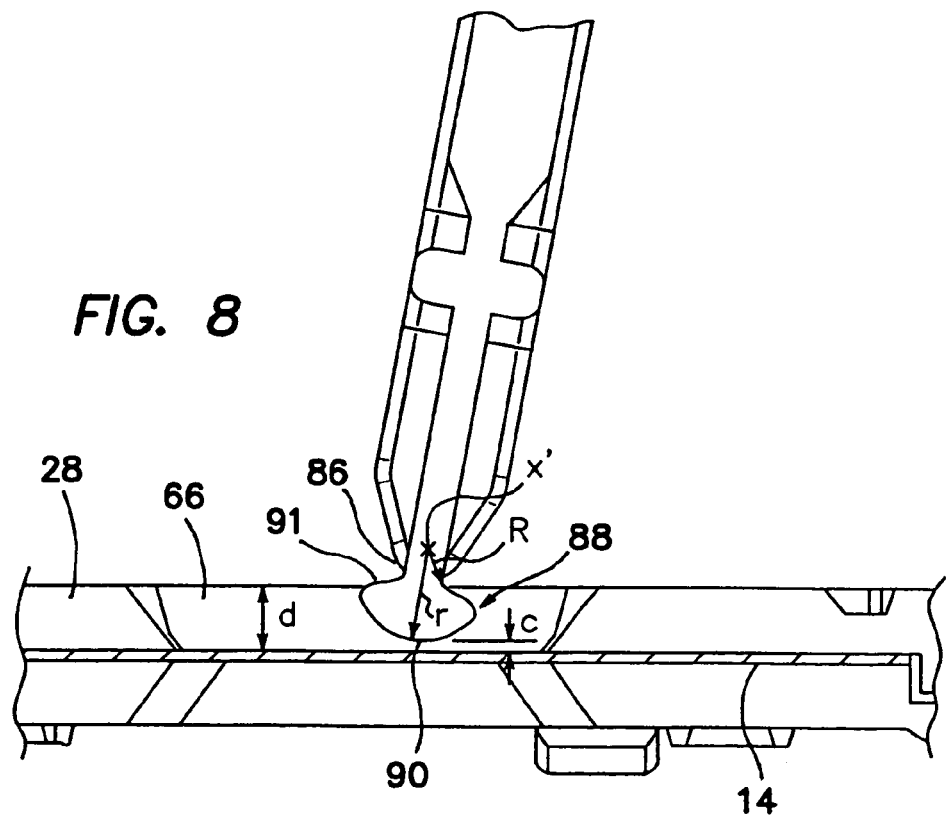
FIG. 8 is an enlarged, fragmentary view of a section taken through line 8—8 of FIG. 1.
Figure 7:
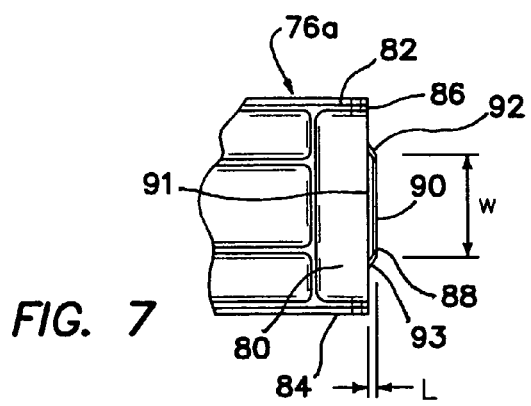
FIG. 7 is a plan view of the encircled area 7—7 of FIG. 5.

Referring now to FIGS. 7–9, the spreader or distal end 76a of the applicator 18 includes a generally planar front surface 80, a generally planar rear surface (not shown) and a pair of side walls 82, 84. The front and rear surfaces are recessed with respect to the side walls 82, 84, and intersect to form a shoulder 86 that curves about a center of curvature x' to define a first radius of curvature R. A spreading tip 88 extends distally of the shoulder 86.

The features of the spreading tip 88 can best be appreciated after considering the design of the specimen placement openings, as shown in detail in FIGS. 4 and 8. Specifically, the specimen placement openings 66, 68 have beveled, generally trapezoidal walls 72 that assist in positioning specimens on the specimen placement area 70 and define a recess with enough volume to receive and hold a fecal sample when the cover 24 is closed. Each recess has a width w equal to the width of the specimen placement area and a depth d equal to the height of the beveled walls 72. The spreading tip 88 includes a pair of side edges 92, 93 which are preferably conical and have a cone angle conforming to the beveled side walls 72 of the specimen placement openings 66, 68. In the most preferred embodiment of the invention, the width w of the distal surface 90 is substantially equal to the width w of the specimen placement openings 66, 68, and the length L of the spreading tip 88 is slightly less than the depth d of the specimen placement openings 66, 68. This close fit between the tip 88 and the specimen placement openings 66, 68 helps ensure that the applicator tip spreads the specimen evenly and thinly over the specimen placement area.

In addition, the spreading tip has a curved distal surface 90 that extends between the side edges 92, 93. The distal surface 90 defines a second radius of curvature r=R+L about the center of curvature x'. Because the spreading tip 88 and the end portion 85 of the applicator have the same center of curvature x', a user is able to maintain a constant distance from the center x' to the test matrix while applying the samples, regardless of moderate changes of the angle at which the applicator 18 is tilted with respect to the test matrix. This results in a constant clearance c between the distal surface 90 of the applicator and the test matrix 14, allowing the user to easily apply the specimen in a layer of fairly uniform thickness.

The distal and proximal surfaces 90, 91 of the spreading tip 88 are preferably textured or otherwise enhanced to increase the amount of fecal matter collected by the applicator 18 and minimize the likelihood of any fecal matter falling off. In the illustrated embodiment, best seen in FIG. 9, the textured surface 90 comprises a multitude of small bumps yielding a sandpaper-like finish. Other surface features, such as grooves, fins, dimples or the like, that increase the effective surface area and holding power of the tip can also be used. Alternatively, the retentiveness of the surface could be enhanced with coatings having adhesive properties or an affinity for fecal matter.

Figure 10:
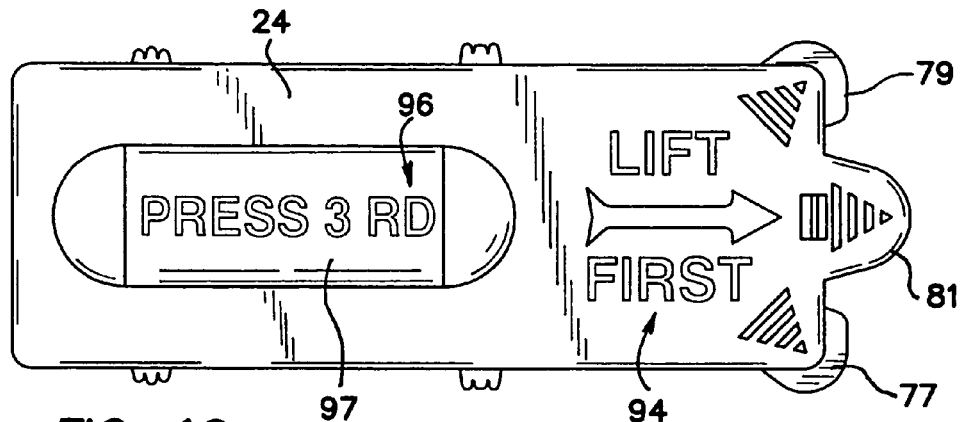
FIG. 10 is a top plan view of the housing of the system according to a preferred embodiment, with the cover in a closed position.

FIGS. 10–12 show an especially preferred embodiment of the invention, wherein the various components of the housing 12 include indicia leading the user through the steps of a testing procedure. The indicia are preferably provided in sets, with each set of indicia designating both the order in which a particular step is to be performed, and the place for performing it. For instance, a first set of indicia 94 provided near the distal end of the cover 24 of the housing 12 may point toward the tab 81 and instruct the user to "LIFT FIRST." Upon lifting the cover, the user may find a second set of indicia 95 near the specimen placement openings 66, 68, instructing him or her to (apply the) "SAMPLES $2^{nd}$." A third set of indicia 96 located on the cover 24 on an upper dome 97 above the ampule-holding dome 74 may instruct the user to "PRESS $3^{rd}$", thus breaking the capsule and releasing the developing medium onto the test matrix. A fourth set of indicia 98 on the bottom section 26 of the housing base 22 identifies the location of the "CONTROLS" and "RESULTS" and instructs the user that these are to be viewed "$4^{th}$."

For optimum readability, it is preferred that the indicia be embossed on the housing. However, imprinted stickers or other less permanent forms of indicia may be preferable in some instances, especially in overseas markets where many languages will be required. Additional indicia could be provided for designating where to snap the applicator halves off the housing, indicating which end of the applicator is the sample end, warning the user not to open the base because of glass inside, and so forth. Of course, the exact wording of any of the instructions is not critical, and may be varied according to consumer needs.

The indicia may also provide information such as a website, mailing address, or phone number which the user may contact if he or she has questions about the procedure or results. If the results are positive or indeterminate, the user may wish to save another undeveloped test kit to show to a physician. Ideally, if the results are clearly negative, the user simply reinserts the kit and applicator halves into the foil pouch in which they were provided, folds over the top of the pouch, and throws it away. No further special handling or sanitary precautions are needed since the fecal matter is entirely enclosed.

While this invention has been described with respect to various specific examples and embodiments, it is to be understood that the invention is not limited thereto and that it can be variously practiced within the scope of the following claims. For instance, the ease of use features disclosed can successfully be used with fecal blood testing kits employing polyclonal or monoclonal antibody systems, or any other alternatives to the guaiac-based chemistry system disclosed in International Patent Application No. PCT/US99/17594. The features may also be used in both chemical and non-chemical systems for revealing the presence of a wider variety of anomalous substances other than blood, such as parasites, for instance, in feces or other spreadable specimens.

What is claimed is:

1. A system for testing for the presence of an anomalous substance in a specimen, the system comprising in combination:

a test matrix having a specimen placement area having a predetermined width and predetermined length;

a housing holding the test matrix and including an opening having a narrowing width profile defined between opposing inwardly angled sidewalls and having a narrow-most width substantially adjacent the specimen placement area; and an applicator for applying a specimen to the specimen placement area, the applicator having a distal tip portion having side edges and a distal tip width defined between the side edges, the width of the distal tip being greater than the narrow-most width of the opening;

the system being structured such that when the applicator distal tip is placed into the housing opening with the side edges of the distal tip in contact with the opposing inwardly angled sidewalls of the opening, a clearance is defined between the applicator distal tip and the specimen placement area.

2. The system according to claim 1, wherein the applicator is releasably coupled to the housing.

3. The system according to claim 1, wherein the applicator comprises:

a handle portion configured to be grasped by a user;

a distal portion; and at least one coupling element on at least one of the handle portion and said distal portion for securing the handle portion to the distal portion.

4. The system according to claim 3, wherein the handle portion is releasably coupled to a first edge of the housing, and the distal portion is releasably coupled to a second edge of the housing.

5. The system according to claim 1, wherein the applicator includes a shoulder portion formed proximally of the distal tip portion, the shoulder portion having a predetermined width greater than the width of the specimen placement area.

6. The system according to claim 1, wherein the distal tip portion has an enhanced surface configured to promote improved retention of a spreadable specimen.

7. The system according to claim 1, wherein the distal tip has a shape promoting enhanced retention of a spreadable specimen.

* * * * *